United States Patent
Brendel et al.

(10) Patent No.: US 8,106,099 B2
(45) Date of Patent: Jan. 31, 2012

(54) COMBINATION OF PHENYLCARBOXAMIDES WITH BLOCKERS OF THE IKR CHANNEL AND THEIR USE FOR THE TREATMENT OF ATRIAL ARRHYTHMIAS

(75) Inventors: Joachim Brendel, Bad Vilbel (DE); Klaus Wirth, Kriftel (DE); Heinz Goegelein, Frankfurt (DE); Maurits Allessie, Maastricht (NL); Yuri Blaauw, Maastricht (NL)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 1093 days.

(21) Appl. No.: 10/796,894

(22) Filed: Mar. 9, 2004

(65) Prior Publication Data
US 2005/0038083 A1   Feb. 17, 2005

Related U.S. Application Data

(60) Provisional application No. 60/492,640, filed on Aug. 5, 2003.

(30) Foreign Application Priority Data

Mar. 18, 2003   (DE) .................................. 10312061

(51) Int. Cl.
*A01N 33/18* (2006.01)
*A01N 33/24* (2006.01)
*A61K 31/04* (2006.01)

(52) U.S. Cl. ....................................................... 514/742
(58) Field of Classification Search .................... 514/742
See application file for complete search history.

(56) References Cited

U.S. PATENT DOCUMENTS 6,531,495 B1 * 3/2003 Brendel et al. ................ 514/357
2002/0161018 A1 * 10/2002 Smith et al. ................... 514/304

OTHER PUBLICATIONS

Prevention, websters online dictionary, www.merriam-webster.com, dated Dec. 11, 2007.*
Prophylaxis, websters online dictionary, www.merriam-webster.com, dated Dec. 11, 2007.*
Lee et al., Atrial flutter: A review of its history, mechanisms, clinical features, and current therapy, Current Problems in Cardiology, vol. 30, Issue 3, Mar. 2005, pp. 121-167.*
U.S. Appl. No. 10/132,163, filed Apr. 26, 2002, Brendel.
U.S. Appl. No. 10/132,184, filed Apr. 26, 2002, Brendel.
U.S. Appl. No. 10/166,595, filed Jun. 12, 2002, Brendel.
Amos, et al., Differences Between Outward Currents of Human Atrial and Subepicardial Ventricular Myocytes, J. Physiology, 191,1; 1996; pp. 31-50.
Brandmeier, et al., Antiparallel b-Sheet Conformation in Cyclopeptides Containing a Pseudo-amino Acid with a Biphenyl Moiety, Helvetica Chimica Acta; 77; 1994; pp. 70-85.
Colatsky, et al., Potassium Channels as Targets for Antiarrhythmic Drug Action, Drug Development Research; 19; 1990; pp. 129-140.
Li, et al., Evidence for Two Components of Delayed Recifier K+ Current in Human Myocytes, Circulation Research, 78,4; 1996; pp. 689-696.
Nattel, Stanley, Newer Developments in the Management of Atrial Fibrillation, Am. Heart J. 130; 1995; pp. 1094-1106.
Roden, Dan M., Current Status of Class III Antiarrhythmic Drug Therapy, Am. J. Cardiology; 72; 1993; pp. 44B-49B.
Wang, at al., Sustained Deplorarization-Induced Outward Current in Human Atrial Myocytes, Circulation Research, 73, 6; 1993; pp. 1061-1076.
Wijffels, et al., Atrial Fibrillation Begets Atrial Fibrillation, Circulation; 92,7; 1995; pp. 1954-1968.
Blaauw, et al., Synergistic class III action of blockade of Ikur/Ito (AVE 0118) and IKr (dofetilide/ibutilide) in electrically remodeled atria of the goat., Circulation Supplement IV; vol. 108; No. 17; Oct. 28, 2003; p. 395.
Brendel, et al., Blockers of the Kv1.5 channel for the treatment of atrial arrhythmias, Expert Opinion on Therapeutic Patents; 12(11); 2002; pp. 1589-1598.
Courtemanche, et al., Ionic Targets for Drug Therapy and Atrial Fibrillation-Induced Electrical Remodeling; Insights From a Mathematical Model, Cardiovascular Research, (1999), 42:477-489.
Peukert, et al., Identification, Synthesis, and Activity of Novel Blockers of the Voltage-Gated Potassium Channel Kv1.5, Journal of Med. Chem.; 46; 4; Feb. 13, 2003; pp. 486-498.

* cited by examiner

Primary Examiner — Frederick Krass
Assistant Examiner — Benjamin Packard
(74) Attorney, Agent, or Firm — Serena Farquharson-Torres; Scully, Scott, Murphy & Presser, P.C.

(57) ABSTRACT

The invention relates to the combination of one or more $IK_r$ channel blockers and of one or more Kv1.5 blockers, in particular phenyl-carboxamides of the formula Ia or Ib

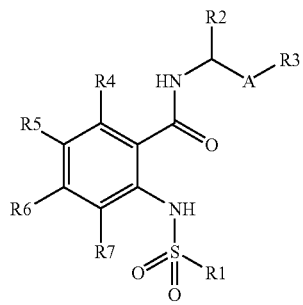

Ia

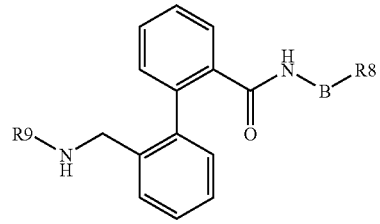

Ib or pharmaceutically tolerable salts thereof, and the use of the combination for the treatment of atrial arrhythmias.

6 Claims, 2 Drawing Sheets

COMBINATION OF PHENYLCARBOXAMIDES WITH BLOCKERS OF THE IKR CHANNEL AND THEIR USE FOR THE TREATMENT OF ATRIAL ARRHYTHMIAS

CROSS-REFERENCE TO RELATED APPLICATIONS

This application claims the benefit of U.S. Provisional Application No. 60/492,640, filed Aug. 5, 2003, and incorporated herein by reference.

DESCRIPTION OF THE INVENTION

The invention relates to the combination of one or more $IK_r$ channel blockers, such as, for example, dofetilide, ibutilide, almokalant, dl-sotalol, d-sotalol, azimilide, amiodarone, E4031, clofilium, ambasilide, MS551, tedisamil, bertosamil or quinidine, and of one or more Kv1.5 blockers, in particular phenylcarboxamides of the formulae Ia and/or Ib and/or pharmaceutically tolerable salts thereof and the use of the combination for the treatment of atrial arrhythmias.

Atrial fibrillation (AF) and atrial flutters are the most frequent, lasting cardiac arrhythmias. The occurrence increases with advancing age and frequently leads to fatal, concomitant symptoms, such as, for example, cerebral infarct. AF affects about 1 million Americans yearly and leads to more than 80,000 strokes each year in the USA. The antiarrhythmics of class I and III customary at present reduce the reoccurrence rate of AF, but are only used restrictively because of their potential proarrhythmic side effects. There is therefore a great medical need for the development of better medicaments for the treatment of atrial arrhythmias (S. Nattel, Am. Heart J. 130, 1995, 1094-1106; "Newer developments in the management of atrial fibrillation").

It has been shown that most supraventricular arrhythmias are subject to "reentry" excitation waves. Such reentries occur when the cardiac tissue possesses a slow conductivity and at the same time very short refractory periods. The increase in the myocardial refractory period due to prolongation of the action potential is a recognized mechanism for ending arrhythmias or preventing their formation (T. J. Colatsky et al., Drug Dev. Res. 19, 1990, 129-140; "Potassium channels as targets for antiarrhythmic drug action"). The length of the action potential is essentially determined by the extent of repolarizing $K^+$ currents which flow out of the cell via various $K^+$ channels. Particularly great importance is ascribed here to the "delayed rectifier" IK, which consists of 3 different components: $IK_r$, $IK_s$ and $IK_{ur}$.

Most known class III antiarrhythmics (for example dofetilide, ibutilide, almokalant and d-sotalol) mainly or exclusively block the rapidly activating potassium channel $IK_r$, which can be detected both in cells of the human ventricle and in the atrium. It has been shown, however, that these compounds have an increased proarrhythmic risk at low or normal heart rates, arrhythmias, which are described as "torsades de pointes", in particular being observed (D. M. Roden, Am. J. Cardiol. 72, 1993, 44B-49B; "Current status of class III antiarrhythmic drug therapy"). Beside this high and in some cases fatal risk at a low rate, a decrease in the activity under the conditions of tachycardia, in which the action is needed in particular, was found for the $IK_r$ blockers ("negative use-dependence").

The "particularly rapidly" activating and very slowly inactivating component of the delayed rectifier $IK_{ur}$ (=ultra-rapidly activating delayed rectifier), which corresponds to the Kv1.5 channel, plays a particularly large part for the repolarization time in the human atrium. An inhibition of the $IK_{ur}$ potassium outward current thus represents, in comparison to the inhibition of $IK_r$ or $IK_s$, a particularly effective method for the prolongation of the atrial action potential and thus for the ending or prevention of atrial arrhythmias.

In contrast to $IK_r$ and $IK_s$, which also occur in the human ventricle, the $IK_{ur}$ in fact plays an important part in the human atrium, but not in the ventricle. For this reason, in the case of inhibition of the $IK_{ur}$ current in contrast to the blockade of $IK_r$ or $IK_s$, the risk of a proarrhythmic action on the ventricle should be excluded from the start. (Z. Wang et al, Circ. Res. 73, 1993, 1061-1076: "Sustained Depolarisation-Induced Outward Current in Human Atrial Myocytes"; G.-R. Li et al., Circ. Res. 78, 1996, 689-696: "Evidence for Two Components of Delayed Rectifier $K^+$-Current in Human Ventricular Myocytes"; G. J. Amos et al, J. Physiol. 491, 1996, 31-50: "Differences between outward currents of human atrial and subepicardial ventricular myocytes").

Antiarrhythmics which act via a selective blockade of the $IK_{ur}$ current or Kv1.5 channel have not been available hitherto on the market. Many patent applications, however, describe compounds which on account of their blocking action on the Kv1.5 channel act as atrial-selective antiarrhythmics. For example, the patent application WO 0125189, inter alia, describes biphenylcarboxamides as Kv1.5 blockers. The applications WO 02088073 and WO 02100825 describe anthranilamides as Kv1.5 blockers for the treatment of arrhythmias.

It has now surprisingly been found that the antiarrhythmic action on the diseased atrium of the heart of Kv1.5 blockers such as, for example, compounds of the formula Ia and Ib can be synergistically enhanced by simultaneous administration of an $IK_r$ channel blocker.

The simultaneous administration of a Kv1.5 blocker with an $IK_r$ channel blocker such as, for example, ibutilide leads in the normal, i.e. healthy, atrium only to an addition of the individual effects. In the fibrillating atrium of the heart, however, in the course of 1 to 4 days a change in the ion channel composition occurs (electric remodeling). Under these conditions, which reflect the situation in the fibrillating patient better than the healthy atrium, the action of the $IK_r$ blocker on its own is markedly reduced. It has surprisingly been found that IK$_r$ channel blockers, which on their own in the remodeled state show a markedly reduced action on the refractory period, again become fully refractory period-active in combination with the IK$_{ur}$ blocker. That is, the blockade of the IK$_{ur}$ obviously restores the action of the IK$_r$ blocker lost in the chronic fibrillation. A combination of an IK$_r$ channel blocker with a Kv1.5 blocker therefore leads to a markedly superadditive enhancing of the action on the atrial effective refractory period (AERP). Since the prolongation of the AERP is a recognized surrogate parameter for the antiarrhythmic action of a substance, the synergistic antiarrhythmic action of the combination is also confirmed hereby.

The surprisingly strong action of the combination on the prolongation of the effective refractory period also leads to a significantly higher success rate in the cardioversion. A persistent fibrillation, i.e. a fibrillation that occurs for even longer than one month, cannot be ended by any known medicament. The IK$_r$ blockers such as, for example, ibutilide or dofetilide on their own lead in this model only to a slight prolongation of the atrial fibrillation cycle length (AFCL), but not to a termination of the fibrillation. Using the Kv1.5 blocker of example 1 on its own, a cardioversion was possible in a dose of, for example, 10 mg/kg. The combination of the compound of example 1 and ibutilide or dofetilide, for example, on the other hand, however, surprisingly led even on administration of the Kv1.5 blocker in doses of, for example, 0.3 to 3 mg/kg together with very low doses (for example 10 µg/kg) of the IK$_r$ channel blocker to a termination of the fibrillation. The combination of the two active principles thus makes possible a marked reduction of the active compound doses to be employed and therewith a considerably improved ratio of desired effects and undesired side effects.

The combinations of Kv1.5 and IK$_r$ blockers described here can therefore be used as highly efficacious antiarrhythmics having a particularly advantageous safety profile. In particular, the compounds are suitable for the treatment of supraventricular arrhythmias, for example atrial fibrillation or atrial flutters. The combinations can be employed for the termination of existing atrial fibrillation or flutters for regaining the sinus rhythm (cardioversion). Owing to the markedly enhanced action of the combination, patients having persistent fibrillation can also be cardioverted, who were previously not accessible to medicinal treatment. Moreover, the combinations reduce the susceptibility to the development of new fibrillation events (retention of the sinus rhythm, prophylaxis).

The invention relates to the combination of one or more IK$_r$ channel blockers and of one or more compounds of the formula Ia and/or Ib Ia Ib in which
R(1) is alkyl having 3, 4 or 5 carbon atoms or quinolinyl,
R(2) is alkyl having 1, 2, 3 or 4 carbon atoms or cyclopropyl;
R(3) is phenyl or pyridyl,
    where phenyl and pyridyl are unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;
A is —C$_n$H$_{2n}$—;
n is 0, 1 or 2;
R(4), R(5), R(6) and R(7)
    independently of one another are hydrogen, F, Cl, CF$_3$, OCF$_3$, CN, alkyl having 1, 2 or 3 carbon atoms, alkoxy having 1, 2 or 3 carbon atoms;
B is —C$_m$H$_{2m}$—;
m is 1 or 2;
R(8) is alkyl having 2 or 3 carbon atoms, phenyl or pyridyl,
    where phenyl and pyridyl are unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;
R(9) is C(O)OR(10) or COR(10);
R(10) is —C$_x$H$_{2x}$—R(11);
    x is 0, 1 or 2;
    R(11) is phenyl,
    where phenyl is unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;
and/or their physiologically tolerable salts.

The combination of one or more IK$_r$ channel blockers and of one or more compounds of the formula Ia and/or Ib and/or physiologically tolerable salts thereof is preferred, the IK$_r$ blockers being selected from the group consisting of dofetilide, ibutilide, almokalant, dl-sotalol, d-sotalol, azimilide, amiodarone, E4031, clofilium, ambasilide, MS551, tedisamil, bertosamil or quinidine.

The combination of one or more IK$_r$ channel blockers and of one or more compounds of the formula Ia and/or Ib and/or physiologically tolerable salts thereof is particularly preferred, the IK$_r$ blockers being selected from the group consisting of dofetilide, ibutilide, almokalant, dl-sotalol, d-sotalol, amiodarone or quinidine.

The combination of one or more IK$_r$ channel blockers and of one or more compounds of the formula Ia and/or Ib and/or physiologically tolerable salts thereof is very particularly preferred, the IK$_r$ blockers being selected from the group consisting of
dofetilide, ibutilide, almokalant, dl-sotalol, d-sotalol, amiodarone or quinidine, and the compounds of the formula Ia and/or Ib being selected from the group consisting of
2'-{[2-(4-methoxyphenyl)acetylamino]methyl}biphenyl-2-carboxylic acid (2-pyridin-3-ylethyl)amide,
2'-(benzyloxycarbonylaminomethyl)biphenyl-2-carboxylic acid 2-(2-pyridyl)-ethylamide, 2'-{[2-(4-methoxyphenyl)acetylamino]methyl}biphenyl-2-carboxylic acid 2,4-difluorobenzylamide, (S)-2'-(α-methylbenzyloxycarbonylaminomethyl)biphenyl-2-carboxylic acid 2-(2-pyridyl)ethylamide, 2-(butyl-sulfonylamino)-N-[1(R)-(6-methoxypyridin-3-yl)propyl]benzamide, 2-(butyl-1-sulfonylamino)-N-(cyclopropylpyridin-3-ylmethyl)-5-methylbenz-amide, (S)-5-fluoro-2-(quinoline-8-sulfonylamino)-N-(1-phenylpropyl)benzamide and/or their physiologically tolerable salts.

The following combinations of IK$_r$ channel blockers and of compounds of the formula Ia and/or Ib are especially preferred, it also being possible for the components to be present in the form of their physiologically tolerable salts:

2'-{[2-(4-methoxyphenyl)acetylamino]methyl}biphenyl-2-carboxylic acid (2-pyridin-3-ylethyl)amide and ibutilide, 2'-{[2-(4-methoxyphenyl)acetylamino]methyl}biphenyl-2-carboxylic acid (2-pyridin-3-ylethyl)amide and dofetilide, 2'-{[2-(4-methoxyphenyl)acetylamino]methyl}biphenyl-2-carboxylic acid (2-pyridin-3-ylethyl)amide and amiodarone, 2-(butyl-1-sulfonylamino)-N-[1 (R)-(6-methoxypyridin-3-yl)propyl]benzamide and ibutilide, 2-(butyl-1-sulfonylamino)-N-[1 (R)-(6-methoxypyridin-3-yl)propyl]benzamide and dofetilide, 2-(butyl-1-sulfonylamino)-N-[1 (R)-(6-methoxypyridin-3-yl)propyl]benzamide and amiodarone, 2-(butyl-1-sulfonylamino)-N-(cyclopropylpyridin-3-ylmethyl)-5-methylbenz-amide and ibutilide, 2-(butyl-1-sulfonylamino)-N-(cyclopropylpyridin-3-ylmethyl)-5-methylbenz-amide and dofetilide,

2-(butyl-1-sulfonylamino)-N-(cyclopropylpyridin-3-ylmethyl)-5-methylbenz-amide and amiodarone, (S)-5-fluoro-2-(quinoline-8-sulfonylamino)-N-(1-phenylpropyl)benzamide and ibutilide,

(S)-5-fluoro-2-(quinoline-8-sulfonylamino)-N-(1-phenylpropyl)benzamide and dofetilide, (S)-5-fluoro-2-(quinoline-8-sulfonylamino)-N-(1-phenylpropyl)benzamide and amiodarone.

Furthermore, the invention relates to the use of one or more IK$_r$ channel blockers together with one or more compounds of the formula Ia and/or Ib Ia Ib for the production of a medicament for the therapy or prophylaxis of atrial fibrillation or atrial flutters, in which R(1) is alkyl having 3, 4 or 5 carbon atoms or quinolinyl, R(2) is alkyl having 1, 2, 3 or 4 carbon atoms or cyclopropyl;

R(3) is phenyl or pyridyl,
where phenyl and pyridyl are unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;

A is —C$_n$H$_{2n}$—;
n is 0, 1 or 2;

R(4), R(5), R(6) and R(7)
independently of one another are hydrogen, F, Cl, CF$_3$, OCF$_3$, CN, alkyl having 1, 2 or 3 carbon atoms, alkoxy having 1, 2 or 3 carbon atoms;

B is —C$_m$H$_{2m}$—;
m is 1 or 2;

R(8) is alkyl having 2 or 3 carbon atoms, phenyl or pyridyl,
where phenyl and pyridyl are unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;

R(9) is C(O)OR(10) or COR(10);

R(10) is —C$_x$H$_{2x}$—R(11);
x is 0, 1 or 2;

R(11) is phenyl,
where phenyl is unsubstituted or substituted by 1 or 2 substituents selected from the group consisting of F, Cl, CF$_3$, OCF$_3$, alkyl having 1, 2 or 3 carbon atoms and alkoxy having 1, 2 or 3 carbon atoms;

and/or their physiologically tolerable salts.

The use of one or more IK$_r$ channel blockers together with one or more compounds of the formula Ia and/or Ib and/or of a physiologically tolerable salt thereof for the production of a medicament for the therapy or prophylaxis of atrial fibrillation or atrial flutters is preferred, the IK$_r$ blockers being selected from the group consisting of dofetilide, ibutilide, almokalant, dl-sotalol, d-sotalol, azimilide, amiodarone, E4031, clofilium, ambasilide, MS551, tedisamil, bertosamil or quinidine.

The use of one or more IK$_r$ channel blockers together with one or more compounds of the formula Ia and/or Ib and/or of a physiologically tolerable salt thereof for the production of a medicament for the therapy or prophylaxis of atrial fibrillation or atrial flutters is particularly preferred, the IK$_r$ blockers being selected from the group consisting of dofetilide, ibutilide, almokalant, dl-sotalol, d-sotalol, amiodarone or quinidine.

The use of one or more IK$_r$ channel blockers together with one or more compounds of the formula Ia and/or Ib and/or of a physiologically tolerable salt thereof for the production of a medicament for the therapy or prophylaxis of atrial fibrillation or atrial flutters is very particularly preferred, the IK$_r$ blockers being selected from the group consisting of dofetilide, ibutilide, almokalant, dl-sotalol, d-sotalol, amiodarone or quinidine and the compounds of the formula Ia and/or Ib being selected from the group consisting of 2'-{[2-(4-methoxyphenyl)acetylamino]methyl}biphenyl-2-carboxylic acid (2-pyridin-3-ylethyl)amide, 2'-(benzyloxycarbonylaminomethyl)biphenyl-2-carboxylic acid 2-(2-pyridyl)-ethylamide, 2'-{[2-(4-methoxyphenyl)acetylamino]methyl}biphenyl-2-carboxylic acid 2,4-difluorobenzylamide, (S)-2'-(α-methylbenzyloxycarbonylaminomethyl)biphenyl-2-carboxylic acid 2-(2-pyridyl)ethylamide, 2-(butyl-1-sulfonylamino)-N-[1 (R)-(6-methoxypyridin-3-yl)propyl]benzamide, 2-(butyl-1-sulfonylamino)-N-(cyclopropylpyridin-3-ylmethyl)-5-methylbenz-amide, (S)-5-fluoro-2-(quinoline-8-sulfonylamino)-N-(1-phenylpropyl)benzamide and/or their physiologically tolerable salts.

The use of the following combinations of $IK_r$ channel blockers together with compounds of the formula Ia and/or Ib for the production of a medicament for the therapy or prophylaxis of atrial fibrillation or atrial flutters is especially preferred, it also being possible for the components to be present in the form of their physiologically tolerable salts:

2'-{[2-(4-methoxyphenyl)acetylamino]methyl}biphenyl-2-carboxylic acid (2-pyridin-3-ylethyl)amide and ibutilide, 2'-{[2-(4-methoxyphenyl)acetylamino]methyl}biphenyl-2-carboxylic acid (2-pyridin-3-ylethyl)amide and dofetilide, 2'-{[2-(4-methoxyphenyl)acetylamino]methyl}biphenyl-2-carboxylic acid (2-pyridin-3-ylethyl)amide and amiodarone, 2-(butyl-1-sulfonylamino)-N-[1 (R)-(6-methoxypyridin-3-yl)propyl]benzamide and ibutilide, 2-(butyl-1-sulfonylamino)-N-[1 (R)-(6-methoxypyridin-3-yl)propyl]benzamide and dofetilide, 2-(butyl-1-sulfonylamino)-N-[1(R)-(6-methoxypyridin-3-yl)propyl]benzamide and amiodarone, 2-(butyl-1-sulfonylamino)-N-(cyclopropylpyridin-3-ylmethyl)-5-methylbenz-amide and ibutilide, 2-(butyl-1-sulfonylamino)-N-(cyclopropylpyridin-3-ylmethyl)-5-methylbenz-amide and dofetilide, 2-(butyl-1-sulfonylamino)-N-(cyclopropylpyridin-3-ylmethyl)-5-methylbenz-amide and amiodarone, (S)-5-fluoro-2-(quinoline-8-sulfonylamino)-N-(1-phenylpropyl)benzamide and ibutilide, (S)-5-fluoro-2-(quinoline-8-sulfonylamino)-N-(1-phenylpropyl)benzamide and dofetilide, (S)-5-fluoro-2-(quinoline-8-sulfonylamino)-N-(1-phenylpropyl)benzamide and amiodarone.

Alkyl radicals and alkylene radicals can be straight-chain or branched. This also applies for the alkylene radicals of the formulae $C_nH_{2n}$, $C_mH_{2m}$ and $C_xH_{2x}$. Alkyl radicals and alkylene radicals can also be straight-chain or branched if they are substituted or are contained in other radicals, for example in an alkoxy radical. Examples of alkyl radicals are methyl, ethyl, n-propyl, isopropyl, n-butyl, isobutyl, sec-butyl, tert-butyl or n-pentyl. The divalent radicals derived from these radicals, for example methylene, 1,1-ethylene, 1,2-ethylene, 1,1-propylene, 1,2-propylene, etc are examples of alkylene radicals.

Pyridyl stands both for 2-, 3- and 4-pyridyl.

Quinolinyl includes 2-, 3-, 4-, 5-, 6-, 7- or 8-quinolyl, the 8-quinolyl radical being preferred.

Monosubstituted phenyl radicals can be substituted in the 2-, the 3- or the 4-position, or disubstituted in the 2,3-, 2,4-, 2,5-, 2,6-, 3,4- or 3,5-position. The same analogously also applies for the pyridyl radicals.

In the case of disubstitution of a radical, the substituents can be identical or different.

If the compounds of the formula Ia or Ib contain one or more acidic or basic groups or one or more basic heterocycles, the invention also includes the corresponding physiologically or toxicologically tolerable salts, in particular the pharmaceutically utilizable salts. Thus, the compounds of the formula Ia can be deprotonated on the sulfonamide group and used, for example, as alkali metal salts, preferably sodium or potassium salts, or as ammonium salts, for example as salts with ammonia or organic amines or amino acids. Compounds of the formula Ia or Ib which contain a pyridine or quinoline substituent can also be used in the form of their physiologically tolerable acid addition salts with inorganic or organic acids, for example as hydrochlorides, phosphates, sulfates, methanesulfonates, acetates, lactates, maleates, fumarates, malates, gluconates etc.

Correspondingly, the $IK_r$ channel blockers can be employed in the form of their physiologically tolerable salts.

In the case of appropriate substitution, the compounds of the formula I can be present in stereoisomeric forms. If the compounds of the formula Ia or Ib contain one or more asymmetric centers, these can independently of one another have the S configuration or the R configuration. The invention includes all possible stereoisomers, for example enantiomers or diastereomers, and mixtures of two or more stereoisomeric forms, for example enantiomers and/or diastereomers, in any desired ratios. Enantiomers, for example, are thus included in enantiomerically pure form, both as levorotatory and as dextrorotatory antipodes, and also in the form of mixtures of the two enantiomers in different ratios or in the form of racemates, in the invention. The preparation of individual stereoisomers can be carried out, if desired, by separation of a mixture according to customary methods or, for example, by use of isomerically pure synthesis units.

Suitable $IK_r$ channel blockers which can be used are, for example, the substances shown in table 1.

TABLE 1

Names and structural formulae of exemplary $IK_r$ channel blockers

| Name | Structure |
|---|---|
| Dofetilide | |

TABLE 1-continued

Names and structural formulae of exemplary IK$_r$ channel blockers

| Name | Structure |
|---|---|
| Ibutilide |  |
| Almokalant |  |
| dl-Sotalol |  |
| d-Sotalol |  |
| Azimilide |  |
| E4031 |  |

TABLE 1-continued

Names and structural formulae of exemplary IK$_r$ channel blockers

| Name | Structure |
|---|---|
| Clofilium |  |
| Ambasilide |  |
| MS551 |  |
| Amiodarone |  |
| Tedisamil |  |
| Bertosamil |  |

TABLE 1-continued

Names and structural formulae of exemplary IK<sub>r</sub> channel blockers

| Name | Structure |
|---|---|
| Quinidine |  |

The compounds of the formulae Ia and Ib used according to the invention and/or their physiologically tolerable salts can thus be used in an advantageous manner as pharmaceuticals together with one or more $IK_r$ channel blockers in animals, preferably in mammals, and in particular in humans, in particular for the treatment of atrial arrhythmias.

The combination of the two active compounds can be carried out in such a way that active compounds of the formula Ia and/or Ib and one or more $IK_r$ channel blockers are administered together in one medicament or that a medicament which contains one or more active compounds of the formula Ia and/or Ib and a separate medicament which contains one or more $IK_r$ blockers are administered simultaneously or successively in any sequence. An administration successively also includes a combination in which the individual medicaments are administered at different times and in different ways in order to achieve a better effect. However, it can also be expedient first to administer a suitable dose of the one medicament and then to administer the other medicament, for example by infusion, until the desired combination effect, for example the cardioversion to the sinus rhythm, has occurred. Depending on the conditions of the individual case, it can be more favorable to administer the active compound(s) of the formula Ia and/or Ib and one or more $IK_r$ channel blockers in the form of a pharmaceutical combination preparation in which the two active compounds are present in a fixed quantitative ratio, or to administer them in the form of separate pharmaceutical individual preparations. In the latter case, in which the quantitative ratio of the two active compounds can be varied, the individual preparations can be situated in suitable primary packaging and, if appropriate, together with use instructions referring to the use according to the invention in a common packaging, or the individual preparations can, if appropriate, in each case be situated in separate packagings together with use instructions referring to the use according to the invention. All products and kinds of preparation of this type are included by the present invention. The invention thus relates, for example, to a product comprising a combination of one or more $IK_r$ channel blockers and of one or more compounds of the formula Ia and/or Ib and/or physiologically tolerable salts thereof for simultaneous, separate or sequential use for the therapy or prophylaxis of atrial fibrillation or atrial flutters.

The weight ratio of the active compounds of the formula Ia and/or Ib to the $IK_r$ channel blocker(s) in the combinations according to the invention is customarily in a range from 10,000:1 to 1:1, preferably between 100:1 and 5:1.

The present invention also relates to the use of compounds of the formulae Ia and/or Ib and/or of a physiologically tolerable salt thereof and of one or more $IK_r$ blockers for the production of pharmaceutical preparations which contain one or more of the compounds Ia and/or Ib and one or more of the $IK_r$ channel blockers as active components in addition to customary, pharmaceutically innocuous vehicles, and their use as a medicament for the treatment of, for example, atrial arrhythmias.

Furthermore, the present invention relates to pharmaceutical preparations (combination preparation) which as active constituent contain an efficacious dose of at least one compound of example Ia and/or Ib and/or of a physiologically tolerable salt thereof and at least one $IK_r$ channel blocker and/or of a physiologically tolerable salt thereof in addition to customary, pharmaceutically innocuous vehicles and excipients and, if appropriate, additionally one or more other pharmacological active compounds. The pharmaceutical preparations normally contain 0.1 to 90% by weight of the compounds of the formulae Ia and/or Ib and/or their physiologically tolerable salts and of the $IK_r$ channel blockers and/or of their physiologically tolerable salts.

The pharmaceutical preparations can be produced in a manner known per se. For this, the active compounds and/or their physiologically tolerable salts, together with one or more solid or liquid pharmaceutical vehicles and/or excipients, are brought into a suitable administration form or dose form, which can then be used as a pharmaceutical in human medicine or veterinary medicine. The same also applies for pharmaceutical preparations which separately contain the two active compounds Kv1.5 blocker and $IK_r$ blocker and/or their pharmaceutically tolerable salts.

Pharmaceuticals which contain combinations of compounds of the formula Ia and/or Ib according to the invention and/or their physiologically tolerable salts and of one or more $IK_r$ blockers and/or their physiologically tolerable salts or the individual components employed in combination can be administered, for example, orally, parenterally, intravenously, rectally, by inhalation or topically, the preferred administration being dependent on the individual case.

In particular, combination preparations of compounds of the formula Ia and/or Ib and/or their physiologically tolerable salts and one or more $IK_r$ blockers and/or their physiologically tolerable salts are claimed for the treatment of atrial arrhythmias such as atrial fibrillation and atrial flutters.

The person skilled in the art is familiar on the basis of his/her expert knowledge with excipients which are suitable for the desired pharmaceutical formulation. In addition to solvents, gel-forming agents, suppository bases, tablet excipients and other active compound carriers, it is possible to use, for example, antioxidants, dispersants, emulsifiers, antifoams, taste corrigents, preservatives, solubilizers, agents for achieving a depot effect, buffer substances or colorants.

For an oral administration form, the active compounds are mixed with the additives suitable therefor, such as vehicles, stabilizers or inert diluents, and brought by means of the customary methods into the suitable administration forms, such as tablets, coated tablets, hard gelatin capsules, aqueous, alcoholic or oily solutions. The inert carriers which can be used are, for example, gum arabic, magnesia, magnesium carbonate, potassium phosphate, lactose, glucose or starch, in particular cornstarch. The preparation can be carried out here both as dry and moist granules. Suitable oily vehicles or solvents are, for example, vegetable or animal oils, such as sunflower oil or cod-liver oil. Suitable solvents for aqueous or alcoholic solutions are, for example, water, ethanol or sugar solutions or mixtures thereof. Further excipients, also for other administration forms, are, for example, polyethylene glycols and polypropylene glycols.

For subcutaneous, intramuscular or intravenous administration, the active compounds, if desired with the substances customary therefor such as solubilizers, emulsifiers or further excipients, are brought into solution, suspension or emulsion. Suitable solvents are, for example, water, physiological saline solution or alcohols, for example ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds or their physiologically tolerable salts in a pharmaceutically innocuous solvent, such as, in particular, ethanol or water, or a mixture of such solvents. If required, the formulation can also additionally contain other pharmaceutical excipients such as surfactants, emulsifiers and stabilizers, and a propellant. Such a preparation customarily contains the active compound in a concentration of approximately 0.1 to 10, in particular of approximately 0.3 to 3, percent by weight.

The dose to be administered according to the invention of the active compounds or of the physiologically tolerable salts thereof depends on the individual case and is to be adapted to the conditions of the individual case as customary for an optimum action. Thus, it depends, of course, on the frequency of administration and on the potency and duration of action of the compounds in each case employed for therapy or prophylaxis, but also on the nature and severity of the illness to be treated and on the sex, age, weight and individual responsiveness of the human or animal to be treated and on whether the therapy is to be acute or chronic or prophylaxis is to be carried out. In particular in the treatment of acute cases of cardiac arrhythmias, for example in an intensive care unit, parenteral administration by injection or infusion, for example by an intravenous continuous infusion, can also be advantageous, when the compounds are used on animals, preferably on mammals, and in particular on humans as medicaments.

The dose of the Kv1.5 blocker of the formula Ia and/or Ib can customarily vary in the range from 1 mg to 1 g per day and per person (in the case of a body weight of approximately 75 kg), preferably from 5 to 750 mg per day per person. In the case of the $IK_r$ blocker, the dose can customarily vary between 1 μg and 10 mg per day per person, preferably between 5 and 500 μg per day per person. However, even higher doses may be appropriate.

In the case of the combination treatment according to the invention, the Kv1.5 blocker(s) and the $IK_r$ blocker(s) and/or their physiologically tolerable salts can be administered in lower doses than in the case of administration of only one of the two active compounds.

In the case of the combination treatment according to the invention, the daily dose of the active compounds can be administered in one portion or it can be divided into a number of, for example two, three or four, administrations.

EXPERIMENTAL SECTION

| List of abbreviations | |
|---|---|
| DMAP | 4-dimethylaminopyridine |
| EDAC | N-ethyl-N'-(3-dimethylaminopropyl)carbodiimide hydrochloride |
| HOBT | 1-hydroxy-1H-benzotriazole |
| RT | room temperature |
| THF | tetrahydrofuran |

Example 1

2'-{[2-(4-Methoxyphenyl)acetylamino]methyl}biphenyl-2-carboxylic acid (2-pyridin-3-ylethyl)amide

15.5 g (0.115 mol) of HOBT and 21.9 g (0.115 mol) of EDAC were added to a solution of 37.8 g (0.11 mol) of 2'-(tert-butoxycarbonylaminomethyl)-biphenyl-2-carboxylic acid (Brandmeier, V.; Sauer, W. H. B.; Feigel, M.; Helv. Chim. Acta 1994, 77(1), 70-85) in 550 ml of THF and the reaction mixture was stirred at room temperature for 45 min. 14.0 g (0.115 mol) of 3-(2-aminoethyl)pyridine were then added and the mixture was stirred overnight at RT. After addition of 400 ml of water and 500 ml of ethyl acetate and intensive stirring, the phases were separated. The organic phase was washed once with 400 ml of saturated sodium chloride solution and twice with 400 ml each of saturated sodium hydrogencarbonate solution. After drying over magnesium sulfate in the presence of activated carbon, it was filtered and concentrated on a rotary evaporator.

The intermediate obtained (40.7 g) was dissolved in 600 ml of methylene chloride and 100 ml of trifluoroacetic acid were then slowly added dropwise. After stirring overnight, the reaction mixture was concentrated in vacuo. The residue was treated with 250 ml of ethyl acetate and concentrated again in order to distill out excess trifluoroacetic acid. 72.8 ml (530 mmol) of triethylamine were added dropwise to the crude product obtained dissolved in 170 ml of methylene chloride and 1 g of DMAP was added. 18.7 g (100 mmol) of 4-methoxyphenylacetyl chloride were then added dropwise at 5-10° C. in the course of 30 min, and the batch was stirred overnight at room temperature. After addition of 150 ml of water and intensive stirring, the phases were separated and the organic phase was washed once with 100 ml of sodium chloride solution, once with 25 ml of 1 M hydrochloric acid and twice with 100 ml each of saturated sodium hydrogencarbonate solution. After drying over magnesium sulfate and activated carbon, it was concentrated in vacuo. The oil obtained was dissolved in hot acetonitrile and slowly allowed to crystallize out. 21.5 g of 2'-{[2-(4-methoxyphenyl)acetylamino]methyl}biphenyl-2-carboxylic acid (2-pyridin-3-ylethyl)amide, melting point 116° C., were obtained.

Example 2

2'-(Benzyloxycarbonylaminomethyl)biphenyl-2-carboxylic acid 2-(2-pyridyl)ethylamide The compound was obtained according to the synthesis procedure indicated in WO 0125189.

Example 3

2'-{[2-(4-Methoxyphenyl)acetylamino]methyl}biphenyl-2-carboxylic acid 2,4-difluorobenzylamide The compound was obtained according to the synthesis procedure indicated in WO 0125189.

Example 4

(S)-2'-(α-Methylbenzyloxycarbonylaminomethyl)biphenyl-2-carboxylic acid 2-(2-pyridyl)ethylamide The compound was obtained according to the synthesis procedure indicated in WO 0125189.

Example 5

2-(Butyl-1-sulfonylamino)-N-[1(R)-(6-methoxypyridin-3-yl)-propyl]benzamide a) 2-(Butyl-1-sulfonylamino)benzoic acid 20 g (188 mmol) of sodium carbonate were added to a suspension of 20 g (146 mmol) of 2-aminobenzoic acid in 250 ml of water. 11.4 g (72.8 mmol) of butylsulfonyl chloride were then added dropwise and the reaction mixture was stirred at room temperature for 2 days. It was acidified with concentrated hydrochloric acid, stirred at room temperature for 3 hours and the deposited product was filtered off with suction. After drying in vacuo, 9.6 g of 2-(butyl-1-sulfonylamino)benzoic acid were obtained.

b) 1-(6-Methoxypyridin-3-yl)propylamine 3 ml (23.2 mmol) of 5-bromo-2-methoxypyridine were added at −70° C. to a solution of 10.2 ml of butyllithium (2.5 M solution in hexane; 25.5 mmol) in 50 ml of diethyl ether. After 10 min, 1.4 ml (19.5 mmol) of propionitrile were added. After 2 hours at −70° C., the reaction mixture was slowly allowed to come to room temperature. 2.2 g of sodium sulfate decahydrate were then added and allowed to stir for 1 hour. After subsequent addition of 5 g of magnesium sulfate, the salts were filtered off after stirring briefly and the filtrate was concentrated. The residue was dissolved in 70 ml of methanol and 1.1 g (28 mmol) of sodium borohydride were added at 0° C. After stirring overnight, the reaction mixture was adjusted to pH 2 using concentrated hydrochloric acid and concentrated on a rotary evaporator. The residue was treated with 10 ml of water, and extracted once with diethyl ether. The aqueous phase was then saturated with sodium hydrogencarbonate, concentrated in vacuo and the residue was extracted with ethyl acetate. After drying and concentrating the ethyl acetate extracts, 1.4 g of racemic 1-(6-methoxypyridin-3-yl)propylamine were obtained.

c) 2-(Butyl-1-sulfonylamino)-N-[1 (R)-(6-methoxypyridin-3-yl)propyl]-benzamide

4.4 g (32.7 mmol) of 1-hydroxy-1H-benzotriazole and 6.3 g (32.7 mmol) of N-ethyl-N'-(3-dimethylaminopropyl)carbodiimide hydrochloride were added to a solution of 8.0 g (31.1 mmol) of 2-(butyl-1-sulfonylamino)benzoic acid in 250 ml of tetrahydrofuran and the reaction mixture was stirred for 90 min. A solution of 5.4 g (32.7 mmol) of racemic 1-(6-methoxypyridin-3-yl)-propylamine in 20 ml of tetrahydrofuran was then added dropwise and the mixture was stirred overnight. The reaction mixture was treated with 250 ml of water and extracted with 300 ml of ethyl acetate. The organic phase was extracted 5 times with 100 ml each of saturated sodium hydrogencarbonate solution and then dried over magnesium sulfate. 9.0 g of 2-(butyl-1-sulfonylamino)-N-[1-(6-methoxypyridin-3-yl)propyl]benzamide were obtained. The enantiomers were separated by preparative HPLC on a Chiralpak ADH column (250×4.6 mm); eluent: heptane/ethanol/methanol 10:1:1; temperature: 30° C.; flow rate: 1 ml/min. First, 4.0 g of 2-(butyl-1-sulfonylamino)-N-[1(R)-(6-methoxypyridin-3-yl)propyl]benzamide were eluted at a retention time of 5.9 min. After a mixed fraction, 3.0 g of 2-(butyl-1-sulfonylamino)-N-[1 (S)-(6-methoxypyridin-3-yl)propyl]benzamide were obtained at a retention time of 7.2 min.

2 g of the 2-(butyl-1-sulfonylamino)-N-[1 (R)-(6-methoxypyridin-3-yl)propyl]-benzamide were dissolved in 9 ml of isopropanol in the presence of heat, then 8 ml of warm water were added and the reaction mixture was slowly allowed to cool overnight. After filtering off with suction at 0° C., 1.5 g of 2-(butyl-1-sulfonylamino)-N-[1 (R)-(6-methoxypyridin-3-yl)propyl]benzamide were obtained as colorless needle-shaped crystals; melting point 97° C.

Example 6

2-(Butyl-1-sulfonylamino)-N-(cyclopropylpyridin-3-ylmethyl)-5-methylbenzamide The compound was obtained according to the synthesis procedure indicated in WO 02088073.

Example 7

(S)-5-Fluoro-2-(quinoline-8-sulfonylamino)-N-(1-phenyl-propyl)benzamide a) 5-Fluoro-2-(quinoline-8-sulfonylamino)benzoic acid A reaction mixture of 10.0 g (64 mmol) of 5-fluoro-2-aminobenzoic acid, 16.3 g (193 mmol) of sodium hydrogencarbonate and 16.3 g of 8-quinoline-sulfonyl chloride in 325 ml of water and 325 ml of ethyl acetate was stirred overnight at RT. The aqueous phase was separated off and extracted once with 50 ml of ethyl acetate. The aqueous phase was then rendered acidic using conc. hydrochloric acid and stirred for 2 h. The precipitate deposited was filtered off with suction, dried in vacuo and 19.5 g of 5-fluoro-2-(quinoline-8-sulfonylamino)benzoic acid were obtained.

b) 5-Fluoro-2-(quinoline-8-sulfonylamino)-N-(1-phenylpropyl)benzamide

From 5.5 g (15.9 mmol) of 5-fluoro-2-(quinoline-8-sulfonylamino)benzoic acid and 2.3 g (16.7 mmol) of (S)-phenylpropylamine, 5.7 g of the title compound were obtained according to the procedure in WO 02100825.

M. p.: 163° C.

Example 8

(S)-5-Fluoro-2-(quinoline-8-sulfonylamino)-N-(1-phenyl-propyl)benzamide sodium salt 2 ml of a 30 percent sodium methoxide solution were added to a solution of 5 g of the compound of example 7 in 120 ml of ethyl acetate. The sodium salt deposited was filtered off with suction and recrystallized from 25 ml of ethanol and 3.3 g of the title compound were obtained.

Pharmacological Investigations

Determination of the Activity on the Kv1.5 Channel

Kv1.5 channels from humans were expressed in *Xenopus* oocytes. For this, oocytes were first isolated from *Xenopus laevis* and defolliculated. RNA encoding Kv1.5 synthesized in vitro was then injected into these oocytes. After Kv1.5 protein expression for 1-7 days, Kv1.5 currents were measured on the oocytes using the two microelectrode voltage clamp technique. The Kv1.5 channels were in this case as a rule activated using voltage jumps to 0 mV and 40 mV lasting 500 ms. The bath was rinsed using a solution of the following composition: NaCl 96 mM, KCl 2 mM, $CaCl_2$ 1.8 mM, $MgCl_2$ 1 mM, HEPES 5 mM (titrated to pH 7.4 using NaOH). These experiments were carried out at room temperature. The following were employed for data acquisition and analysis: Geneclamp amplifier (Axon Instruments, Foster City, USA) and MacLab D/A converter and software (ADInstruments, Castle Hill, Australia). The substances according to the invention were tested by adding them to the bath solution in different concentrations. The effects of the substances were calculated as percentage inhibition of the Kv1.5 control current which was obtained when no substance was added to the solution. The data were then extrapolated using the Hill equation in order to determine the inhibitory concentrations $IC_{50}$ for the respective substances.

In this manner, the following $IC_{50}$ values were determined for the compounds listed below:

| Example No. | $IC_{50}$ [μM] |
| --- | --- |
| 1 | 4.7 |
| 2 | 0.7 |
| 3 | 1.4 |
| 4 | 0.2 |
| 5 | 10 |
| 6 | 1.0 |
| 7 | 1.1 |

Investigation of the Refractory Period in Normal Goats and in Goats with Remodeled Atria The electrophysiological effects of the compound of example 1, of the $IK_r$ channel blocker ibutilide and of the combination of the compound of example 1 and ibutilide were investigated in chronically instrumented goats. The experiments were carried out on normal atria of healthy goats, and on atria in which an "electrical remodeling" was present as a result of an atrial fibrillation existing for 1-4 days. This electrical remodeling, which reflects the situation in the patient, was achieved by repetitive atrial stimulations as published by Wijffels et al. (Atrial fibrillation begets atrial fibrillation. A study in awake chronical instrumented goats. Circulation 1995, 92, 1954-68).

After infusion of 0.9% saline solution for 30 min as a control, the substances ibutilide and the compound of example 1 were administered by intravenous infusion to 7 normal goats (i.e. without induced atrial fibrillation) on the one hand in monotherapy and on the other hand in combination of the two active compounds and the atrial effective refractory period (AERP) was determined. In the monotherapy, 0.12 mg of ibutilide per kg of bodyweight was administered over the length of time of 60 minutes (0.002 mg per kg per minute). In the combination, 6 mg of the compound of example 1 per kg of bodyweight were administered over the time of 120 minutes (3 mg per kg per hour), where after 60 minutes 0.12 mg of ibutilide per kg per hour was additionally administered for the period of 60 minutes. The infusion of the compound of example 1 was carried out altogether for 120 min. Control measurements of the atrial effective refractory period were carried out once before administration of the ibutilide (control 1) and once before administration of the compound of example 1 (control 2).

The results of the measurements of the atrial effective refractory period (AERP) with a cycle length of 400 ms in normal (a) and remodeled (b) atria of 7 goats are summarized in table 1. Ibutilide on its own prolonged the AERP by 26 ms (n=7) and the compound of example 1 by 47 ms (n=7). These prolongations were statistically significant (p<0.001) relative to the control values 159 ms and 162 ms (in each case before substance administration). The combination of both substances was tested by additionally administering ibutilide for one hour as described above after the infusion of the compound of example 1. An increase in the AERP by 75 ms (n=7) resulted after the combined administration. It is seen that in the case of combined administration the effects are additive.

The same infusion scheme was repeated on the same animals after electrical remodeling had been produced by induced atrial fibrillation of 1 to 4 days. The results are summarized in table 1. It can be seen that in these animals the AERP under control conditions was only 93 ms and 97 ms respectively (n=7). After administration of ibutilide, the prolongation of the AERP was 5 ms (n=7) and that of compound of example 163 ms (n=7). After combined administration, an increase in the AERP by 94 ms (n=7) was observed.

TABLE 1

Mean value ± SD of the effective atrial refractory periods, measured on 7 animals.

|  | Control 1 (ms) | Ibutilide (ms) | Control 2 (ms) | Compound of example 1 (ms) | Compound of example 1 + ibutilide (ms) |
|---|---|---|---|---|---|
| Non-remodeled | 159 ± 16 | 185 ± 23 | 162 ± 23 | 206 ± 26 | 234 ± 31 |
| Remodeled | 93 ± 18 | 98 ± 20 | 97 ± 19 | 160 ± 16 | 191 ± 28 |

A similar infusion scheme was carried out on 5 further animals with dofetilide instead of ibutilide. After infusion of 0.9% saline solution for 30 min as control, the substances dofetilide and the compound of example 1 were administered by intravenous infusion to 5 normal goats (i.e. without induced atrial fibrillation) on the one hand in monotherapy and on the other hand in combination of the two active compounds and the atrial effective refractory period (AERP) was determined. In the monotherapy, 0.12 mg of dofetilide per kg of bodyweight was administered over the length of time of 60 minutes (0.002 mg per kg per minute). In the combination, 6 mg of the compound of example 1 per kg of bodyweight were administered over the time of 120 minutes (3 mg per kg per hour), where after 60 minutes 0.12 mg of dofetilide per kg per hour was additionally administered for the period of 60 minutes. The infusion of the compound of example 1 was carried out altogether for 120 min. Control measurements of the atrial effective refractory period were carried out once before administration of the dofetilide (control 1) and once before administration of the compound of example 1 (control 2).

The results of the measurements of the atrial effective refractory period (AERP) with a cycle length of 400 ms in normal (a) and remodeled (b) atria of 7 goats are summarized in table 2. Dofetilide on its own prolonged the AERP by 21 ms (n=5) and the compound of example 1 by 51 ms (n=5). These prolongations were statistically significant (p<0.001) relative to the control values 151 ms and 158 ms (in each case before substance administration). The combination of both substances was tested by additionally administering dofetilide for one hour as described above after the infusion of the compound of example 1. An increase in the AERP by 75 ms (n=5) resulted from the combined administration. It is seen that in the case of combined administration the effects are additive.

The same infusion scheme was repeated on the same animals after electrical remodeling had been produced by induced atrial fibrillation of 1 to 4 days. The results are summarized in table 2. It can be seen that in these animals the AERP under control conditions was only 94 ms and 93 ms (n=5) respectively. After administration of dofetilide, the prolongation of the AERP was 7 ms (n=5) and that of compound of example 171 ms (n=5). After combined administration, an increase in the AERP by 91 ms (n=5) was observed.

TABLE 2

Mean value ± SD of the effective atrial refractory periods, measured on 5 animals.

|  | Control 1 (ms) | Dofetilide (ms) | Control 2 (ms) | Compound of example 1 (ms) | Compound of example 1 + dofetilide (ms) |
|---|---|---|---|---|---|
| Non-remodeled | 151 ± 8 | 172 ± 11 | 158 ± 15 | 209 ± 29 | 234 ± 30 |
| Remodeled | 94 ± 17 | 101 ± 19 | 93 ± 19 | 164 ± 19 | 184 ± 23 |

The following can thus be seen from these experiments. The positive effect on the AERP with administration of ibutilide or dofetilide is markedly lower in remodeled atrium than in normal atrium. This effect is markedly greater in the case of the administration of the compound of example 1 in remodeled atrium than in normal atrium. In the case of the combined administration of ibutilide and the compound of example 1, the effect on the AERP in remodeled atrium is markedly greater than in the normal atrium and also markedly greater than additive effects of the two individual active compounds, which demonstrates the synergistic action of the combination.

Investigation of Cardioversion in Chronically Fibrillating Goats

Experiments were carried out on two goats which were in persistent atrial fibrillation of more than 45 days. After infusion of 0.9% saline solution for 30 min as a control, the compound of example 1 was infused into a goat in succession (in each case at an interval of days) in amounts of in each case 0.0 (control), 0.1, 0.3, 1, 3 and 10 mg per kg of bodyweight and per hour for a period of 90 minutes, where 2 mg of ibutilide per kilogram of bodyweight was additionally administered after 60 minutes in a time interval of 30 min.

Analogously, after administration of various amounts of the compound of example 1 for 60 minutes (in each case 0.0 (control), 0.1, 0.3, 1, 3 and 10 mg per kg of bodyweight and per hour (in each case in an interval of days), 10 μg of dofetilide per kg of bodyweight were additionally administered to a second goat in a time interval of 30 min instead of ibutilide.

The times of the cardioversion of persistent atrial fibrillation (AF) due to the administration of the compound of example 1 with ibutilide or of the compound of example 1 with dofetilide are shown in tables 3 and 4 at various doses of the compound of example 1 (0.0, 0.1, 0.3, 1, 3 and 10 mg per kg of bodyweight and per hour).

TABLE 3

Occurrence of the cardioversion of persistent atrial fibrillation (AF) after reinduction in each case of the atrial fibrillation with various doses of the compound of example 1 and with additional infusion of ibutilide after 60 minutes (times in minutes measured from the beginning of the infusion of the compound of example 1)
Dose of the compound of example 1

| 0 mg/kg/h | 0.1 mg/kg/h | 0.3 mg/kg/h | 1 mg/kg/h | 3 mg/kg/h | 10 mg/kg/h |
|---|---|---|---|---|---|
| | | | Times (min) | | |
| | | | 82.00 | 71.00 | 65.55 | 42.00 |
| | | | 88.00 | 71.30 | 68.10 | 50.00 |
| | | | | 72.00 | 68.20 | 74.24 |
| | | | | 74.00 | 69.49 | 74.30 |
| | | | | 77.00 | 69.55 | 74.34 |
| | | | | 79.00 | 70.50 | 74.42 |
| | | | | 81.00 | 71.26 | 74.50 |
| | | | | 81.10 | 71.43 | 74.58 |
| | | | | 82.10 | 71.56 | 75.10 |
| | | | | 84.00 | 72.09 | 76.55 |
| | | | | 84.30 | 72.20 | 77.00 |
| | | | | 84.50 | 72.36 | 77.30 |
| | | | | 85.00 | 73.14 | 77.35 |
| | | | | 85.30 | 74.00 | 77.40 |
| | | | | | 74.20 | 78.10 |
| | | | | | 74.29 | 78.20 |
| | | | | | 74.39 | 78.30 |
| | | | | | 75.00 | 78.35 |
| | | | | | 75.10 | 78.48 |
| | | | | | 75.40 | 79.10 |
| | | | | | 75.43 | 79.20 |
| | | | | | 75.48 | 79.30 |

TABLE 4

Occurrence of the cardioversion of persistent atrial fibrillation (AF) after reinduction in each case of the atrial fibrillation with various doses of the compound of example 1 and with additional infusion of dofetilide after 60 minutes (times in minutes measured from the beginning of the infusion of the compound of example 1)
Dose of the compound of example 1

| 0 mg/kg/h | 0.1 mg/kg/h | 0.3 mg/kg/h | 1 mg/kg/h | 3 mg/kg/h | 10 mg/kg/h |
|---|---|---|---|---|---|
| | | | | Times (min) | |
| | | | | 65.50 | 83.00 |
| | | | | 66.10 | 83.30 |
| | | | | 70.57 | 84.30 |
| | | | | 73.45 | 84.37 |
| | | | | 73.55 | 85.22 |
| | | | | 74.30 | 85.34 |
| | | | | 75.20 | 85.47 |
| | | | | 75.50 | 85.50 |
| | | | | 76.40 | 85.58 |
| | | | | 79.40 | 86.14 |
| | | | | 80.40 | |
| | | | | 81.09 | |
| | | | | 81.30 | |

Figure 1:
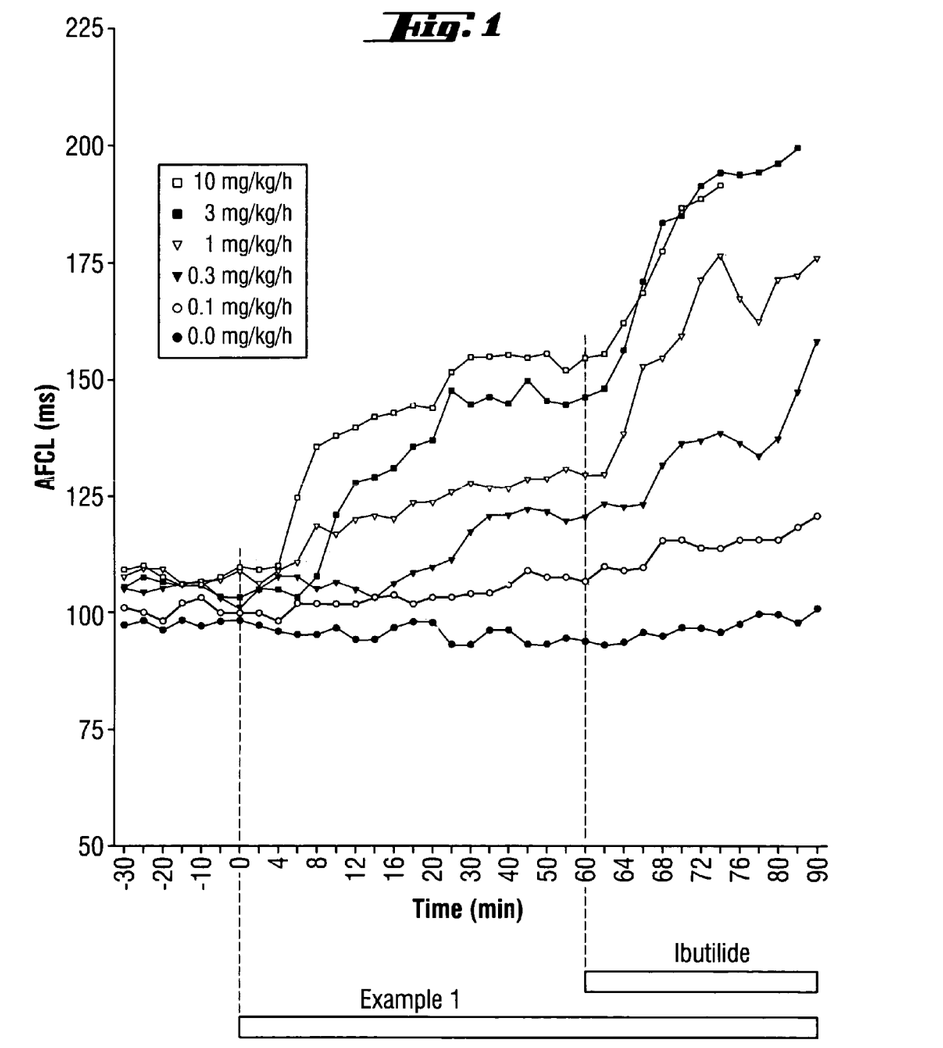
FIG. 1: Measurement of the atrial fibrillation cycle length (AFCL) after combined administration of ibutilide and of the compound of example 1
Y axis: AFCL in ms
X axis: time in minutes
The compound of example 1 was infused in the following amounts:
10 mg/kg/h
3 mg/kg/h
1 mg/kg/h
0.3 mg/kg/h
0.1 mg/kg/h
0.0 mg/kg/h (control).
Figure 2:
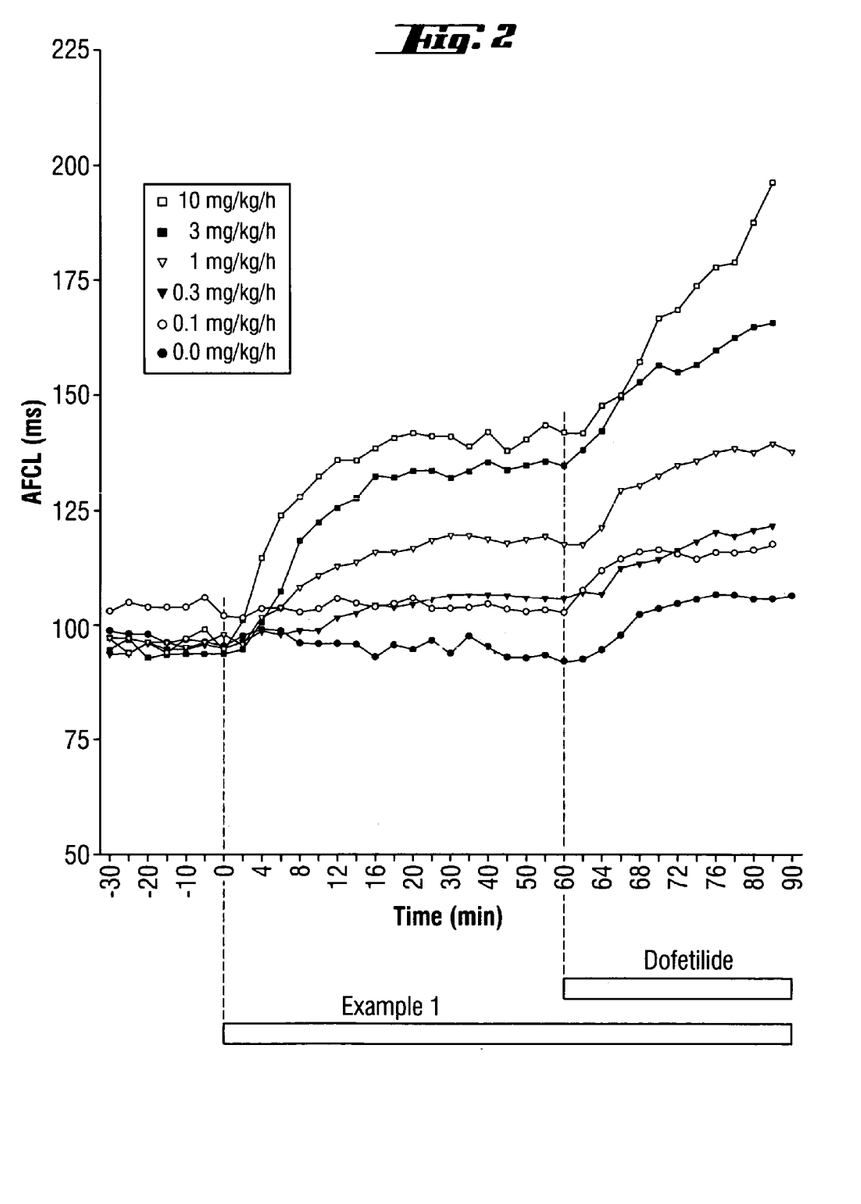
FIG. 2: Measurement of the atrial fibrillation cycle length (AFCL) after combined administration of dofetilide and of the compound of example 1
Y axis: AFCL in ms
X axis: time in minutes
The compound of example 1 was infused in the following amounts:
10 mg/kg/h
3 mg/kg/h
1 mg/kg/h
0.3 mg/kg/h
0.1 mg/kg/h
0.0 mg/kg/h (control).

The measurements of the atrial fibrillation cycle length (AFCL) after combined administration of ibutilide and of the compound of example 1 or after combined administration of dofetilide and of the compound of example 1 are shown in FIG. 1 and FIG. 2. The measurements of the AFCL and of the cardioversion were carried out successively.

Tables 3 and 4 demonstrate, just like FIGS. 1 and 2, that the administration of saline solution, i.e. of 0.0 mg of compound of example 1 per kg of bodyweight and per hour, causes no significant effect with respect to the AFCL and the cardioversion.

Ibutilide on its own leads to only a very small increase in the AFCL from 94 ms to 101 ms (FIG. 1, 0.0 mg/kg/h, administration of ibutilide after 60 minutes). After treatment with 3 mg of the compound of example 1 per kg of bodyweight per hour, the same dose of ibutilide (2 mg per kg of bodyweight per 30 minutes) prolongs the AFCL by 50 ms (from 147 ms to 197 ms). In the monotherapy with the compound of example 1, it was only possible by administration of 10 mg of the compound of example 1 per kg of bodyweight per hour to bring about a cardioversion (table 3). In contrast to this, in the case of the combination with ibutilide even the relatively low doses of 0.3, 1 and 3 mg of the compound of example 1 per kg of bodyweight per hour led to the termination of the atrial fibrillation (table 3).

Similar results were obtained with dofetilide. FIG. 2 and table 4 show that after infusion of 10 μg of dofetilide per kg of bodyweight for 30 min without the compound of example 1 the AFCL only increases by 14 ms (from 92 ms to 106 ms) and a cardioversion does not occur. The infusion of the compound of example 1 in the various doses (0.1, 0.3, 1, 3 or 10) on its own leads to a dose-dependent increase in the AFCL, but not to cardioversion. Only with the combination of the compound of example 1 and dofetilide do the doses of 3 and 10 mg of the compound of example 1 per kg of bodyweight and per hour bring about a termination of the atrial fibrillation (table 4).

From these experiments, it can thus be seen that a combination of the compound of example 1 with ibutilide or dofetilide at low doses of the compound of example 1 and very low doses of ibutilide or dofetilide leads to a cardioversion and thus to a termination of the fibrillation.

Further tests were carried out to test the efficiency of cardioversion at various doses of the compound of example 1 and at additional infusion of ibutilide (2 mg/kg) or dofetilide (10 µg/kg) on several goats (table 5).

Experiments were carried out on up to eight goats which were in persistent atrial fibrillation. After infusion of 0.9% saline solution for 30 min as a control, the compound of example 1 was infused in up to eight goats (in each case at an interval of days) in amounts of in each case 0.0 (control), 0.1, 0.3, 1.3 and 10 mg per kg of bodyweight and per hour for a period of 90 minutes, where 2 mg of ibutilide per kilogram of bodyweight were additionally administered after 60 minutes in a time interval of 30 min.

Analogously, after administration of various amounts of the compound of example 1 for 60 minutes to up to eight goats (in each case 0.0 (control), 0.1, 0.3, 1, 3 and 10 mg per kg of bodyweight and per hour in each case in an interval of days) 10 µg of dofetilide per kg of bodyweight were additionally administered in a time interval of 30 min instead of ibutilide.

The efficiency of the cardioversion of persistent atrial fibrillation (AF) due to the administration of the compound of example 1 with ibutilide or of the compound of example 1 with dofetilide is shown in table 5 at various doses of the compound of example 1 (0.0, 0.1, 0.3, 1, 3 and 10 mg per kg of bodyweight and per hour). The reported numbers indicate the number of goats where cardioversion occurred versus the number of goats on which the experiment was carried out and, calculated therefrom, the efficiency of cardioversion in percent. Each termination of persistent atrial fibrillation during any one infusion period was deemed to be an instance of successful cardioversion. Infused for one hour at 3 mg/kg/h, for example, the compound of example 1 led to AF termination in 3 of 8 goats. When example 1 (3 mg/kg/h) was administered in combination with ibutilide, AF was terminated in 6 of 7 goats. At 10 mg/kg of the compound of example 1, persistent atrial fibrillation was successfully terminated in every goat on additional infusion of ibutilide or dofetilide.

TABLE 5

Efficiency of cardioversion in percent in goats with persistent atrial fibrillation (AF) at various doses of the compound of example 1 and with additional infusion of ibutilide or dofetilide. The numbers in parentheses each indicate the ratio of goats where cardioversion occurred to goats used in the particular experiment.

| Compound of example 1 (mg/kg) | Efficiency of cardioversion | | |
| --- | --- | --- | --- |
| | Monotherapy | +ibutilide (2 mg/kg) | +dofetilide (10 µg/kg) |
| 0 | 0% (0/8) | 29% (2/7) | 25% (1/4) |
| 0.1 | 17% (1/6) | 33% (1/3) | 33% (1/3) |
| 0.3 | 17% (1/6) | 50% (2/4) | 0% (0/2) |
| 1 | 13% (1/8) | 75% (3/4) | 50% (2/4) |
| 3 | 38% (3/8) | 86% (6/7) | 75% (3/4) |
| 10 | 63% (5/8) | 100% (5/5) | 100% (4/4) |

DESCRIPTION OF THE DRAWINGS

The following captions and markings were made in the drawings, which are graphical representations.

What is claimed is:

1. A pharmaceutical preparation for treating atrial arrhythmia in a mammal, said preparation comprising a combination of:
    2'-{[2-(4-methoxyphenyl)acetylamino]methyl}biphenyl-2-carboxylic acid (2-pyridin-3-ylethyl)amide and ibutilide in a weight ratio of 10,000:1 to 1:1; or
    or the physiologically tolerable salts thereof,
    and a pharmaceutically innocuous solvent, wherein the preparation provides an hourly dose of 3 mg per kg of said 2'-{[2-(4-methoxyphenyl)acetylamino]methyl}biphenyl-2-carboxylic acid (2-pyridin-3-ylethyl)amide when administered to said mammal.

2. The pharmaceutical preparation of claim 1 wherein the preparation provides an hourly dose of 0.12 mg per kg of said ibutilide when administered to said mammal.

3. The pharmaceutical preparation of claim 1, wherein said weight ratio is 100:1 to 5:1.

4. A pharmaceutical preparation for treating atrial arrhythmia in a mammal, said preparation comprising a combination of:
    2'-{[2-(4-methoxyphenyl)acetylamino]methyl}biphenyl-2-carboxylic acid (2-pyridin-3-ylethyl)amide and dofetilide in a weight ratio of 10,000:1 to 1:1; or
    or the physiologically tolerable salts thereof,
    and a pharmaceutically innocuous solvent, wherein the preparation provides an hourly dose of 3 mg per kg of said 2'-{[2-(4-methoxyphenyl)acetylamino]methyl}biphenyl-2-carboxylic acid (2-pyridin-3-ylethyl)amide when administered to said mammal.

5. The pharmaceutical preparation of claim 4 wherein the preparation provides an hourly dose of 0.12 mg per kg of said dofetilide when administered to said mammal.

6. The pharmaceutical preparation of claim 4, wherein said weight ratio is 100:1 to 5:1.

* * * * *